United States Patent [19]

Nadelson

[11] 4,032,644

[45] June 28, 1977

[54] ISOXAZOLYL BENZOIC ACIDS

[75] Inventor: Jeffrey Nadelson, Lake Parsippany, N.J.

[73] Assignee: Sandoz, Inc., E. Hanover, N.J.

[22] Filed: Dec. 29, 1975

[21] Appl. No.: 645,023

[52] U.S. Cl. .......................... 424/272; 260/307 H; 260/307 F
[51] Int. Cl.² ................ C07D 263/32; A61K 31/42
[58] Field of Search ............... 260/307 H, 307 F; 424/272

*Primary Examiner*—Donald G. Daus
*Assistant Examiner*—D. B. Springer
*Attorney, Agent, or Firm*—Gerald D. Sharkin; Robert S. Honor; Timothy G. Rothwell

[57] ABSTRACT

Substituted or unsubstituted isoxazolyl benzoic acids, e.g. o-(4-methyl-3-phenylisoxazol-5-yl)benzoic acid, are prepared by dehydrating a corresponding 5-hydroxy-2-isoxazolin-5-yl benzoic acid, and are useful as hypolipidemic agents.

6 Claims, No Drawings

ISOXAZOLYL BENZOIC ACIDS

This invention relates to isoxazolyl benzoic acids which exhibit hypolipidemic activity. More particularly, it relates to substituted or unsubstituted isoxazolyl benzoic acids, intermediates thereof, pharmaceutically acceptable salts and to processes for their preparation.

The compounds of this invention may be represented by the following structural formula:

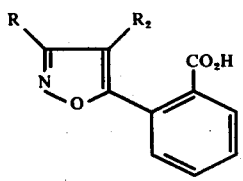

where
R represents t-butyl or $R_1$

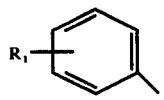

and $R_1$ represents hydrogen, halo having an atomic weight of about 19 to 36, lower alkyl, i.e. alkyl having 1 to 4 carbon atoms, e.g. methyl, ethyl, isopropyl and the like, or lower alkoxy, i.e. alkoxy having 1 to 4 carbon atoms, e.g. methoxy, ethoxy, isopropoxy and the like, and $R_2$ represents hydrogen or straight chain lower alkyl, i.e. straight chain alkyl having 1 to 4 carbon atoms, e.g. methyl, ethyl, propyl and the like.

The compounds of formula (I) are prepared according to the following reaction scheme:

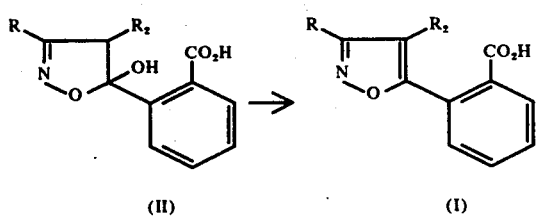

where R and $R_2$ are as defined above.

The compounds of formula (I) are prepared by dehydrating a compound of the formula (II) with a dilute inorganic aqueous acid in the presence of water. The particular inorganic aqueous acid employed is not critical but it is preferred that the reaction be carried out in the presence of sulfuric acid, hydrochloric acid, phosphoric acid and the like, preferably sulfuric acid. The temperature at which the reaction is carried out is not critical, but it is preferred that the reaction be run at about 80° to 150° C., preferably at the reflux temperature of the reaction medium. The time of the reaction also is not critical, but it is preferred that the reaction be run for 12 to 30 hours, preferably 16 to 24 hours. The compounds of formula (I) are recovered using conventional techniques, e.g. trituration.

The compounds of formula (II) may be prepared in accordance with the following reaction scheme:

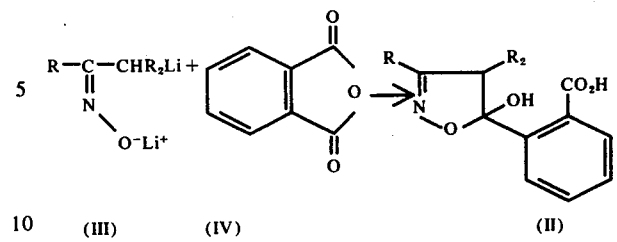

where R and $R_2$ are as defined above.

The compounds of formula (II) are prepared by treating a compound of the formula (III) with a compound of the formula (IV) in the presence of an inert organic solvent. Although the particular solvent used is not critical, it is preferred that the reaction be carried out in the presence of an ether such as diethylether, dioxane, tetrahydrofuran and the like, or an aliphatic hydrocarbon such as heptane, hexane and the like, preferably tetrahydrofuran. The temperature of the reaction is not critical, but it is preferred that the reaction be carried out at a temperature between about −70° to −40° C., preferably from about −65° to −55° C. The reaction may be run from about 1 to 5 hours, preferably from about 2 to 4 hours. The compounds of formula (II) are not isolated but employed in situ in the preparation of the compounds of formula (I).

The compounds of formula (III) are prepared according to the following reaction scheme:

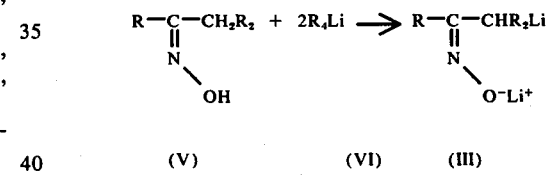

where $R_4$ is lower alkyl having 1 to 4 carbon atoms, and R and $R_2$ are as defined above.

The compounds of formula (III) are prepared by treating a compound of the formula (V) with a compound of the formula (VI) in an inert solvent. Although the particular inert solvent used is not critical, it is preferred that the reaction be carried out in the presence of an ether, such as diethylether, dioxane, tetrahydrofuran and the like, or an aliphatic hydrocarbon such as hexane, heptane, and the like, preferably tetrahydrofuran. The temperature at which the reaction is run is not critical, but is is preferred that the reaction may be carried out between about −20° to +20° C., preferably between about −5° to +5° C. The time of the reaction also is not critical, but it is preferred that the reaction be run for 30 minutes to 4 hours, especially 1 to 2 hours. The compounds of formula (III) are normally employed in the solvent in which they are prepared for preparing the compounds of formula (II).

It is to be noted that the compounds of formula (II) also exist in the following tautomeric forms and said tautomeric forms are also included within this invention. For convenience, however, reference in the claims and text will be made only to compounds of the formula (II).

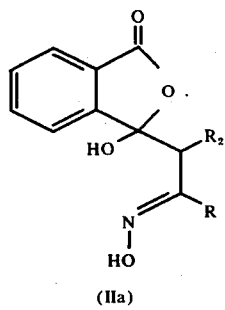 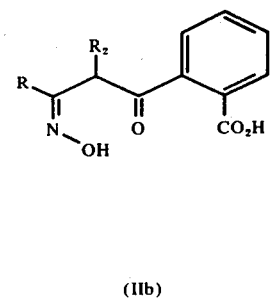

(IIa)  (IIb)

where R and $R_2$ are as defined above.

The compounds of formulae (I) and (II) may similarly exist in the form of their non-toxic pharmaceutically acceptable salts. Such salts are readily prepared by reacting the acid with an appropriate base by conventional techniques, and are included within the scope of this invention. Representative of such salts are the alkali metal salts, including potassium, lithium, sodium and the like.

Many of the compounds of formulae (V) and (VI) are known and may be prepared by methods described in the literature. The compounds of formulae (V) and (VI) not specifically described may be prepared by analogous methods from known starting materials.

The compounds of formula (I) are useful because they possess pharmacological activity in animals as hypolipidemic agents, as indicated by the fall in cholesterol and triglyceride levels in male albino Wistar rats weighing 110–130 g. initially. The rats are maintained on drug-free laboratory chow diet for seven days and then divided into gorups of 8 to 10 animals. Each group with the exception of the control is then given orally 30 to 150 milligrams per kilogram of body weight per diem of the compound for six days. At the end of this period, the animals are anethetized with sodium hexobarbital and bled from the carotid arteries. Serum or plasma samples are collected, and 1.0 ml. samples of the serum are added to 9.0 ml. redistilled isopropanol. Two autoanalyzer cupsful of a mixture of zeolite-copper hydroxide and Lloydds reagent (Kessler, G., and Lederer, H., 1965, Technicon Symposium, Mediad Inc., New York, 345–347. are added, and the mixture is shaken for one hour. Cholesterol and triglyceride levels are determined simultaneously on the same sample by Technicon N 24 A (cholesterol) and N-78 (triglyceride) methodology. The mean total serum cholesterol levels are then computed and the hypocholesterolemic activity is expressed as the fall in cholesterol levels as a percentage of the control level. The change in serum triglyceride levels induced by the drug is computed as a percentage of the control triglyceride levels.

For such usage, the compounds (I) may be combined with a pharmaceutically acceptable carrier or adjuvant and may be administered orally or parenterally as such or admixed with conventional pharmaceutical carriers. They may be administered in such forms as tablets, dispersible powders, granules, capsules, syrups, and elixirs and parenterally as solutions, suspensions, dispersions, emulsions and the like, e.g., a sterile injectable aqueous solution. The dosage will vary depending upon the mode of administration utilized and the particular compound employed.

The hypolipidemic effective dosage of compounds (I) employed in the alleviation of lipidemia may vary depending on the particular compound employed and the severity of the condition being treated. However, in general, satisfactory results are obtained when the compounds of formula (I) are administered at a daily dosage of from about 10.0 milligrams to about 250 milligrams per kilogram of animal body weight, preferably given in divided doses two to four times a day, or in sustained release form. For most large mammals, the total daily dosage is from about 600 milligrams to about 1500 milligrams. Dosage forms suitable for internal use comprise from about 150 to about 750 milligrams of the active compound in intimate admixture with a solid or liquid pharmaceutically acceptable carrier or diluent.

The compounds of formula (I) may be similarly administered in the form of their non-toxic pharmaceutically acceptable salts. Such salts possess the same order of activity as the free acid.

A representative formulation suitable for oral administration 2 to 4 times a day for the treatment of lipidemia is a capsule prepared by standard encapsulating techniques which contain the following:

| Ingredient | Weight (mg) |
| --- | --- |
| o-(4-methyl-3-phenylisoxazol-5-yl)benzoic acid | 150 |
| inert solid diluent (starch, lactose, kaolin) | 300. |

EXAMPLE 1 o-(4-methyl-3-phenylisoxazol-5-yl)benzoic acid

A solution of 30.0 g. (0.200 mole) of propiophenone oxime in 600 ml. dry tetrahydrofuran is cooled to 0° C. and then treated dropwise with 275 ml. (0.440 mole) n-butyllithium (1.6 m in hexane). The addition is completed after about 30 minutes. After the addition, the mixture is stirred for one hour at room temperature and then cooled to −60° C., and treated dropwise with 29.6 g. (0.200 mole) of phthalic anhydride in 250 ml. of dry tetrahydrofuran. The resulting mixture is stirred for 3 hours at −60° C., warmed to −30° C., and quenched with 2N hydrochloric acid. The resulting layers are separated and the organic phase dried over anhydrous magnesium sulfate, filtered and evaporated in vacuo to give a residue containing o-(5-hydroxy-4-methyl-3-phenyl-2-isoxazolin-5-yl)benzoic acid.

The residue is then suspended in 500 ml. 2M sulfuric acid and refluxed for 18 hours. The mixture is cooled and methylene chloride added and then filtered to remove insoluble material. The organic phase is then dried over anhydrous magnesium sulfate, filtered and evaporated in vacuo. The residue is then triturated with ether to give o-(4-methyl-3-phenylisoxazol-5-yl)benzoic acid; m.p. 159° to 161° C.

Following the above procedure and using in place of propiophenone oxime an equivalent amount of
  a. acetophenone oxime,
  b. p-chloropropiophenone oxime,
  c. p-fluoropropiophenone oxime,
  d. p-methylpropiophenone oxime,
  e. p-methoxypropiophenone oxime, and
  f. pinacolone oxime
there is obtained
  a. o-(5-hydroxy-3-phenyl-2-isoxazolin-5-yl) benzoic acid.

b. o-(5-hydroxy-4-methyl-3-p-chlorophenyl-2-isoxazolin-5-yl)benzoic acid,
c. o-(5-hydroxy-4-methyl-3-p-fluorophenyl-2-isoxazolin-5-yl)benzoic acid,
d. o-(5-hydroxy-4-methyl-3-p-tolyl-2-isoxazolin-5-yl)benzoic acid,
e. o-(5-hydroxy-4-methyl-3-p-anisyl-2-isoxazolin-5-yl)benzoic acid, or
f. o-(5-hydroxy-4-methyl-3-t-butyl-2-isoxazolin-5-yl)benzoic acid, respectively.

Again following the above procedure and using in place of o-(5-hydroxy-4-methyl-3-phenyl-2-isoxazolin-5-yl) benzoic acid an equivalent amount of
a. o-(5-hydroxy-3-phenyl-2-isoxazolin-5-yl)benzoic acid,
b. o-(5-hydroxy-4-methyl-3-p-chlorophenyl-2-isoxazolin-5-yl)benzoic acid,
c. o-(5-hydroxy-4-methyl-3-p-fluorophenyl-2-isoxazolin-5-yl)benzoic acid,
d. o-(5-hydroxy-4-methyl-3-p-tolyl-2-isoxazolin-5-yl)benzoic acid,
e. o-(5-hydroxy-4-methyl-3-p-anisyl-2-isoxazolin-5-yl)benzoic acid, or
f. o-(5-hydroxy-4-methyl-3-p-t-butyl-2-isoxazolin-5-yl)benzoic acid,
there is obtained
a. o-(3-phenylisoxazol-5-yl)benzoic acid,
b. o-(4-methyl-3-p-chlorophenylisoxazol-5-yl) benzoic acid,
c. o-(4-methyl-3-p-fluorophenylisoxazol-5-yl) benzoic acid,
d. o-(4-methyl-3-p-tolylisoxazol-5-yl)benzoic acid,
e. o-(4-methyl-3-p-anisylisoxazol-5-yl)benzoic acid, or
f. o-(4-methyl-3-t-butylisoxazol-5-yl)benzoic acid, respectively.

The o-(4-methyl-3-phenylisoxazol-5-yl)benzoic acid is an effective hypolipidemic agent when orally administered to an animal suffering from lipidemia at a dosage of 150 mg. four times per day.

What is claimed is:
1. A compound of the formula

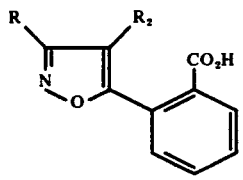

where
R represents t-butyl or $R_1$

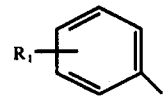

and
$R_1$ represents hydrogen, fluoro or chloro, lower alkyl having 1 to 4 carbon atoms, or lower alkoxy having 1 to 4 carbon atoms, and
$R_2$ represents hydrogen or straight chain lower alkyl having 1 to 4 carbon atoms
or a pharmaceutically acceptable salt thereof.

2. A compound of the formula

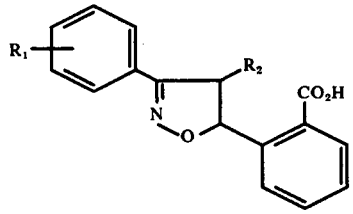

where $R_1$ and $R_2$ are as defined in claim 1 or a pharmaceutically acceptable salt thereof.

3. The compound of claim 2 which is o-(4-methyl-3-phenylisoxazol-5-yl)benzoic acid.

4. A compound of the formula

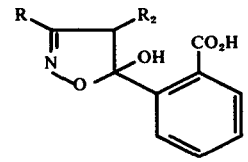

where R and $R_2$ are as defined in claim 1.

5. A pharmaceutical composition comprising an amount of a compound of claim 1 effective in the treatment of lipidemia and a pharmaceutically acceptable carrier or diluent therefor.

6. A method of treating lipidemia which comprises administering to a mammal in need of said treatment a hypolipidemic effective amount of a compound of claim 1.

* * * * *